(12) United States Patent
Lang

(10) Patent No.: US 6,263,243 B1
(45) Date of Patent: Jul. 17, 2001

(54) RATE ADAPTIVE PACEMAKER

(75) Inventor: Martin Lang, Grossenseebach (DE)

(73) Assignee: Biotronik Mess-und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 08/810,024

(22) Filed: Mar. 4, 1997

(30) Foreign Application Priority Data

Mar. 4, 1996 (DE) .............................. 196 09 382

(51) Int. Cl.⁷ .................................................. A61N 1/365
(52) U.S. Cl. ................................. 607/17; 607/18
(58) Field of Search ............................ 607/9, 17–19, 607/24

(56) References Cited

U.S. PATENT DOCUMENTS

| | | | |
|---|---|---|---|
| 4,535,774 | * 8/1985 | Olson ..................................... | 607/24 |
| 5,074,302 | 12/1991 | Poore et al. . | |
| 5,190,035 | * 3/1993 | Salo et al. .............................. | 607/24 |
| 5,303,702 | 4/1994 | Bonnet et al. . | |

FOREIGN PATENT DOCUMENTS

| | | |
|---|---|---|
| 3419439 | 11/1985 | (DE) . |
| 41 11 505 A1 | 10/1992 | (DE) . |
| 0325851 | 8/1989 | (EP) . |
| 0576114 A2 | 12/1993 | (EP) . |
| 0616819 A2 | 2/1994 | (EP) . |
| 0654285 | 5/1995 | (EP) . |

OTHER PUBLICATIONS

Max Schaldach: "Electrotherapy of the Heart". Springer Verlag, pp. 114–121.
Chu–Pak Lau: "The Range of Sensors and Algorithms Used in Rate Adaptive Cardiac Pacing". In: PACE, vol. 15, Aug. 1992, pp. 1177–1211.

\* cited by examiner

Primary Examiner—William E. Kamm
Assistant Examiner—George R. Evanisko
(74) Attorney, Agent, or Firm—Venable; Robert Kinberg

(57) ABSTRACT

A rate-adaptive pacemaker includes an impedance measuring device for measuring a waveform over time of the intracardial impedance over at least a predetermined portion of one cardiac cycle. An impedance processing device obtains an impedance value from the waveform. A rate determining device is connected downstream of the impedance processing device, and controlled by a sequence controller, determines the adaptive stimulation rate (HR) using the impedance value. The impedance processing device has an integrator stage for determining the time integral of the impedance waveform over the predetermined portion of the cardiac cycle as the primary impedance value.

12 Claims, 3 Drawing Sheets

RATE ADAPTIVE PACEMAKER

Pacemakers that adjust the adaptive heart rate as a function of exertion on the part of the person with the pacemaker are known.

German Patent DE C 34 19 439 describes a pacemaker that with a temperature probe measures the blood temperature of the venous blood in the heart and adjusts the adaptive heart rate as a function of the measured value. This principle is based on the finding that the blood temperature of the human being rises upon exertion. The association of the blood temperature with the physiologically appropriate adaptive heart rate is effected by means of the characteristic curve that allocates one value of the adaptive heart rate to each value of the blood temperature.

A disadvantage of this known pacemaker is that the relationship between the blood temperature and the physiologically appropriate heart rate is as a rule different for each purpose, so that the pacemaker must be calibrated individually for each person with the pacemaker.

Moreover, an exertion-dependent change in the blood temperature—for instance from aging of the temperature probe or if the temperature probe shifts in the body of the person with the pacemaker—also causes a change in the adaptive heart rate, which is physiologically inappropriate.

Many arrangements for measuring impedance in the area of the thorax or in the heart to obtain an impedance signal for rate-adaptive pacemakers are known, and thus the technique of intracardial impedance measurement is familiar per se to one skilled in the art. However, the goal of most of these arrangements is a finding on the tidal volume or cardiac output, as an expression of the physical exertion of the patient and as the actual rate control parameter.

The so-called ResQ method (for Regional Effective Slope Quality) is also known (Max Schaldach, Electrotherapy of the Heart, First Edition, Springer-Verlag, page 114 ff.), in which the course of intracardial impedance over time is utilized to determine the physiologically appropriate adaptive heart rate.

This process is based on the finding that the intracardial impedance, in a particular time window after a QRS complex—the so-called "region of interest" (ROI)—has an especially significant dependency on the exertion of the organism.

The slope of the impedance curve in the ROI is therefore determined, and the difference between the slope of a resting or reference curve and the slope of the currently measured impedance curve (exertion curve) is calculated. Depending on this difference, the adaptive heart rate is set. The association of the calculated slope difference with the heart rate to be set is effected here as well by means of a characteristic curve. Since this relationship is different as a rule for different people, the pacemaker must be calibrated individually for each person, and the calibrations must be repeated if the state of health and exertion capacity change or if the living conditions of the patient change, and then the position of the ROI must also be checked.

SUMMARY OF THE INVENTION

It is therefore an object of the invention in particular to create a pacemaker of the generic type in question that can make do without a patient-specific calibration operation and that adapts automatically to altered peripheral conditions.

The invention encompasses the concept of utilizing the course over time—which because of the linkages via the autonomic nervous system (ANS) is an excellent reflection of the overall exertion situation (physical exercise and psychic stress) of a patent—of the intracardial (and in particular right-ventricle) impedance in a conclusive variable that does not require individual-patient adjustment for the purposes of rate adaptation.

The pacemaker according to the invention evaluates the intracardial impedance, in particular the right-ventricle impedance measured in a unipolar fashion over a wide range, which includes the ROI regions typically established for individual patients. In this region it determines a relationship between a resting or reference curve and an exertion curve, especially by way of an arithmetic processing of the time integral of the impedance over the aforementioned range.

To that end, the output of the integrator stage is connected in particular to an integral value memory, in which one reference integral value at a time, ascertained in at least one preceding cardiac cycle, is stored in memory; and the rate determining device has an arithmetic unit, connected to the output of the integrator stage and the integral value memory, for calculating a secondary impedance variable from the respective primary impedance variable and from the reference integral value in accordance with a predetermined arithmetical equation. In an advantageously simple version, the arithmetic unit has a subtraction stage for forming the differential value between the primary impedance variable and the reference integral value—but some other arithmetic processing may also be done, or optionally a multistage threshold value discrimination as well.

Defining the time range or integration limits requires no patient-individual programming after implantation; instead, these limits can be stored, particularly upon manufacture of the pacemaker, in a read-only memory (ROM) connected (at least indirectly) to one control input of the integrator stage. The limits of the predetermined portion are ascertained as the result of the investigations of the range, relevant to the rate adaptation, of the course over time of the impedance in a patient population.

The aforementioned resting or reference curve is preferably "carried over", that is, averaged from impedance values obtained over a predetermined period of time of several (for instance, three) minutes; either a sliding averaging or averaging for successive separate periods of time may be done. As a result, rapid adaptation to changing peripheral conditions—such as stimulation parameters, medication or living habits—is attained, and the threat to the patient that would be caused if the pacemaker became stuck at physiologically excessively high rates is avoided.

Upon a transition from spontaneous to stimulated heart activity (upon an increase in exertion) or vice versa, the current impedance curve at the time is expediently defined as the new reference curve. To avoid sudden changes in rate, however, the rate should not be changed at that moment, or should be changed only insignificantly, which requires the introduction of a rate offset amount, which is then gradually reduced again over a predetermined time or a predetermined number of cardiac cycles. Realizing these functions is achieved—along with a suitable embodiment of the pacemaker or sequence controller—by a control connection with the output stage and by an offset memory.

Expanded functionality is offered by equipping the pacemaker with a sensor for an activity variable connected at least indirectly to a control input of the integrator stage and/or a control input of the rate determining device, the output signal of which sensor sets at least one of the limits of the integration range and/or a characteristic curve member of the rate determining device. As an especially simple and also expedient sensor, a digital motion sensor can be considered, which in particular accomplishes a switchover between various programmed time range or integration limits and/or a corresponding switchover of the processing characteristic (characteristic curve) of the rate determining device.

In a further specialized embodiment, the rate determining device includes a differential member that has a data input for the impedance value, with which very long changes in impedance can be rendered inoperative for the pacemaker control. As a result—with drastically reduced calculation effort and current consumption—a similar effect is attained to that accomplished with the carrying over of the impedance resting curve.

In an expedient further development, the differential member has a time constant control input connected to the sensor for the activity variable, by way of which input the differential time is set to a value that is substantially lower in the resting state than when the patient is active. If a digital motion sensor—already mentioned above—is used, then the adjustment or setting is effected in particular as a switchover between preset time constants.

The characteristic curve, which determines the dependency of the stimulation rate on the impedance measuring device and is the essential operating parameter of the rate determining device, is preferably not static but instead is optimized continuously or at certain time intervals. The goal of the optimization is first to adapt the variation range of the impedance measuring device to the allowable variation range of the heart rate.

The variation range is not known at the onset of operation but instead is ascertained by continuous measurement of the impedance during operation and is optimized after each measurement. At the onset of operation, an estimate is specified as a starting value for the lower and upper limits of the variation range.

In the optimization, two cases can be distinguished: On the one hand, the case can occur that a measured value of the impedance either exceeds or undershoots the variation range ascertained thus far. In that case, the variation range is widened accordingly and thus updated. The growth time constant of this adaptation operation is preferably on the order of magnitude of a few seconds, to achieve rapid adaptation and thus to prevent an excessively increased heart rate. On the other hand, the case can occur where the impedance no longer fully exhausts the previously determined variation range over a relatively long period of time. In one embodiment of the invention, the variation range is therefore slowly reduced again in that case. The time constant of this adaptation operation is preferably on the order of magnitude of several weeks.

The characteristic curve is adapted during the optimization to the current value of the variation range of the activity variable (the impedance). Thus the characteristic curve assigns the base rate to the lower limit value of the variation range of the activity variable and correspondingly assigns the maximum stimulation rate to the upper value of the activity variable. Thus if these limit values change during the optimizing, the characteristic curve changes as well.

In an advantageous variant, the calculated adaptive heart rate is therefore evaluated statistically. From the statistical distribution within the allowable variation range from the base rate up to the maximum stimulation rate, information can be obtained for optimizing the characteristic curves. For each patient, as a function of his exertion profile and other factors, a physiologically appropriate statistical distribution of the activity variable can be determined, in the form of a frequency distribution function, in that the course of the characteristic curve is adjusted between the coordinate points such that the frequency distribution function of the adaptive heart rate comes as close as possible to the physiologically appropriate frequency distribution function.

The characteristic curve can for instance be realized as a polynomial, and then the characteristic curve is determined in its entirety by the coefficients of the polynomial, as follows:

$$HR(A) = K_0 + K_1 \cdot A + K_2 \cdot A^2 + K_3 \cdot A^3 + \ldots$$

The coefficients $K_i$ are then determined such that on the one hand the corresponding limit values of the allowable variation range of the heart rate are assigned to the limit values of the variation range of the activity variable, and on the other the frequency distribution function of the adaptive heart rate comes as close as possible to the physiologically appropriate frequency distribution function.

Accordingly, the following must be true:

$$HR(A_{MIN}) = TR$$

$$HR(A_{MAX}) = MSR$$

$$V(HR) = V_{REF}$$

where $A_{MIN}$, $A_{MAX}$ are limit values of the variation range of the activity variable TR is the target rate (base rate)

MSR is the maximum stimulation rate

V is the frequency distribution function of the heart rate, and $V_{REF}$ is the physiologically appropriate frequency distribution function.

To calculate the frequency distribution function of the adaptive heart rate, the entire allowable variation range is for instance divided into equidistant frequency intervals, and for each frequency interval the time is determined within which the heart rate was within the frequency interval during an observation period. To suppress the influence of cyclical fluctuations in the adaptive heart rate over the daily or weekly cycle, the duration of observation here is preferably on the order of magnitude of several weeks.

When the activity sensor and differential member are combined, the following mode of operation in particular results: If the motion sensor detects motion on the part of the person with the pacemaker, then the differential time $T_D$ and the differential transmission factor $K_D$ of the differential member are increased equally markedly. As a result of the increase in differential time TD it is attained that even relatively long-lasting exertions are supported with an increased heart rate. By the simultaneous increase in the differential constant $K_D$, the steadiness of the output signal of the differential member is assured. If this were not done, the output signal of the differential member would jump if the differential time $T_D$ were to change, which would be physiologically inappropriate. Once the physical exertion ends, the differential time $T_D$ and the differential transmission factor $K_D$ are returned again to the values they had before the exertion phase.

Advantageous further features of the invention will be described in further detail below along with a preferred embodiment of the invention, in conjunction with the drawings.

BRIEF DESCRIPTION OF THE DRAWINGS

Shown are.

DETAILED DESCRIPTION OF THE INVENTION

Figure 1:
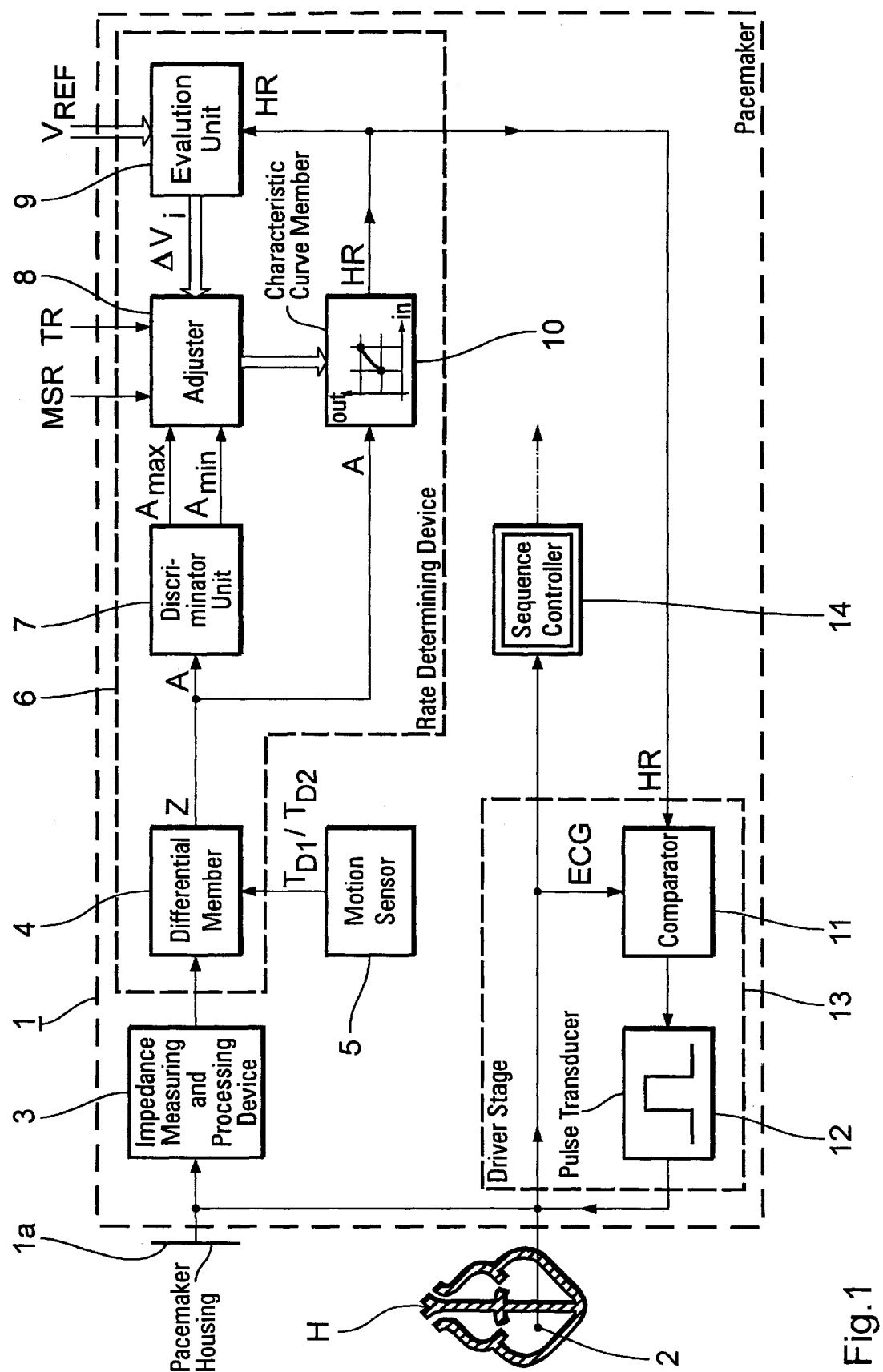
FIG. 1, a pacemaker as an exemplary embodiment of the invention, in the form of a block circuit diagram.

FIG. 1, as the exemplary embodiment of the invention, shows a rate-adaptive pacemaker 1 as a functional block circuit diagram; only the components important for explaining the invention are shown.

The impedance measuring device and impedance processing device 3, via a unipolar measuring electrode 2 in the right ventricle of the heart H, measures the right-ventricle intracardial impedance Z. The measurement is effected in clocked fashion, in that a measuring voltage is imposed on the measuring electrode 2, and the current between the measuring electrode 2 and the pacemaker housing 1a, acting as a counterelectrode, is measured at eight equidistant times within a fixedly preprogrammed time range. The impedance Z is the quotient of the measuring voltage and the current. The clock frequency of the impedance measurement here is from some tens of a Hertz to approximately 100 Hertz. As a result, in accordance with the well known scanning theorem, it is attained that the discrete-time impedance signal is an adequately good representation of the actual course of the impedance Z.

The impedance Z exhibits relatively major variations during a cardiac cycle. As a result, at the onset of a cardiac cycle the impedance Z is minimal immediately after a QRS complex and then rises again until the next QRS complex; its course over time, after integration and arithmetic processing—as described in further detail herein after in conjunction with FIG. 4—furnishes the rate setting parameter.

Downstream of the measuring and processing device 3 is a rate determining device 6 which produces an adaptive heart rate HR at its output. Rate determining device 6 includes a differential member 4 having a differential time $T_D$. This differential member 4 has the task of filtering out slow changes in the intracardial impedance Z, whose time constant is above the differential time $T_D$.

In addition to the impedance measuring device, a motion sensor 5 is provided, which, as a function of the state of motion of the person with the pacemaker, furnishes a binary signal (motion yes/no). As a function of this motion signal, the differential time $T_D$ of the differential member 4 is adjusted. In the resting state of the person with the pacemaker, a differential time $T_{D1}=10$ min is set. This means that variations in the impedance Z whose time constant is greater than 10 min do not lead to a relevant change in the adaptive heart rate. If the motion sensor detects motion on the part of the person with the pacemaker that is associated with physical exertion, then the differential time is set to $T_{D2}=5$ h.

The rate determining device 6 futher includes a characteristic curve member 10, which by means of a characteristic curve assigns a value of the adaptive heart rate HR to each value of the impedance variable A—which is post processed in the differential member. The characteristic curve is adjusted and optimized continuously during operation of the pacemaker by means of an adjuster 8, in that the processing of the impedance variable is adapted to the allowable variation range of the heart rate HR, which is predetermined by a base rate TR as the lower limit value and a maximum stimulation rate MSR as the upper limit value.

The variation range of the activity variable A is determined by a discriminator unit 7, which continuously determines the maximum $A_{MAX}$ and the minimum $A_{MIN}$ of the impedance variable during the past four weeks.

The characteristic curve K (see FIG. 2) is realized in the characteristic curve member as a polygonal course with a total of 12 equidistant coordinate points. One coordinate point is defined by the lower limit value $A_{MIN}$ of the variation range of the processed impedance variable and by the base rate TR, and a second coordinate point is defined by the upper limit value $A_{MAX}$ of the variation range of the impedance variable and by the maximum stimulation rate MSR, and the equations given above apply. The location of the remaining (in this example, ten) coordinate points can be derived from a further optimizing goal, which is to adapt the frequency distribution function V of the adaptive heart rate HR as well as possible to a reference curve $V_{REF}$ (see FIG. 3).

The adaptive heart rate HR is therefore statistically evaluated by an evaluation unit 9. To that end, the frequency distribution function V of the adaptive heart rate HR is determined continuously. How this is done is that for each of the 11 frequency intervals $\Delta HR_i$, located between the 12 coordinate points of the characteristic curve K, the percentage of time within an observation period for which the adaptive heart rate HR was within this frequency interval $\Delta HR_i$ is determined. The frequency distribution function V ascertained is compared with a reference curve $V_{REF}$, which represents a physiologically appropriate frequency distribution function of the adaptive heart rate HR. To that end, the difference $\Delta V_i$, between the measured frequency distribution function V and the reference curve $V_{REF}$ is formed at each of the coordinate points $V_i$ and supplied to the adjuster 8.

If the measured frequency distribution function V and the reference curve $V_{REF}$ match, this means that the characteristic curve is optimally adapted. If not, the characteristic curve K is optimized by the adjuster 8. If the frequency distribution function V of the heart rate is above the reference curve $V_{REF}$ in the frequency interval between the first and second coordinate points of the characteristic curve, this means that heart rates occur overly often within this frequency interval. The slope dHR/dA of the characteristic curve should therefore be increased in this frequency interval. To that end, the second coordinate point is shifted toward the first coordinate point in the direction of decreasing activity values. Conversely, if the frequency distribution function V is below the reference curve $V_{REF}$, this means that heart rates within this frequency interval occur too seldom. The slope dHR/dA of the characteristic curve should therefore be reduced in that frequency interval. To that end, the second coordinate point is shifted relative to the first coordinate point in the direction of increasing activity values.

In the same way, the new location of the other coordinate points is determined. If the frequency distribution function V is above the reference curve $V_{REF}$ in a frequency interval located between two coordinate points, then the coordinate point belonging to the higher frequency is shifted in the direction of decreasing activity or impedance variable values.

The control device is followed by a driver or output stage 13 for stimulating the heart. The pacemaker 1 operates on the demand principle; that is, it stimulates the heart only whenever within a certain waiting period after a preceding contraction of the heart no contraction from any natural stimulation occurs. The driver stage 13 therefore has a comparator unit 11, which via the measuring electrode 2 picks up the electrocardiogram (ECG) at the heart 1 and determines the natural heart rate from this and compares it with the adaptive heart rate. If within the waiting period after a preceding contraction no natural contraction of the heart 1 is detected, then the comparator unit 11 triggers a pulse transducer 12, which emits an electrical stimulation pulse to the stimulating electrode 2 (acting simultaneously as a measuring electrode.

To control the general pacemaker functions and to perform the impedance measurement and processing, a sequence controller (controller) 14 that includes a time base is provided; it outputs control signals (represented symbolically by a single arrow) to the function components.

Figure 2:
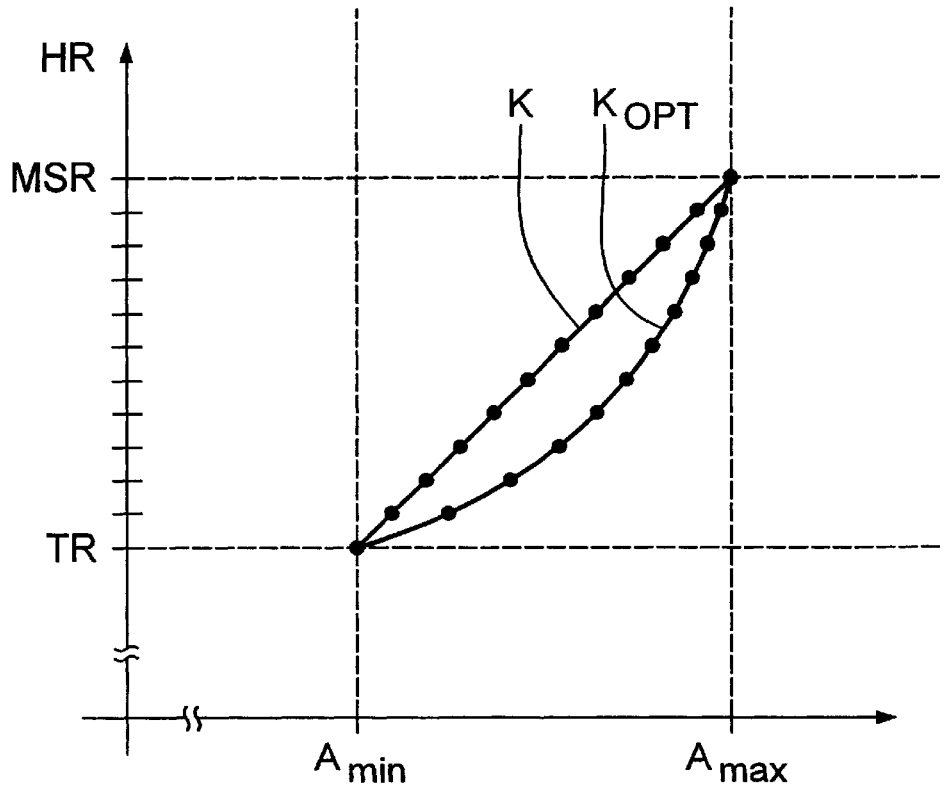
FIG. 2, a characteristic curve and an optimized characteristic curve for the association of the activity variable with the adaptive heart rate in the pacemaker shown in FIG. 1.

FIG. 2 as an example shows the characteristic curve K of the characteristic curve member 10 of FIG. 1 along with an optimized characteristic curve $K_{OPT}$. The characteristic curve K is formed by a polygonal course with a total of 12 coordinate points and assigns one value of the adaptive heart rate HR to each value of the variation range of the activity variable from $A_{MIN}$ to $A_{MAX}$.

The limit values of the variation range of the activity variable A are not constant here. Instead, the pacemaker "learns" continuously during operation what variation range results given the exertion occurring in the daily life of the person with the pacemaker. The variation range of the activity variable A is accordingly redetermined continuously. Hence the location of the characteristic curve K varies as well.

The lower limit value $A_{MIN}$ of the variation range of the activity variable A and the base rate TR form one coordinate point, while the upper limit value $A_{MAX}$ of the variation range of the activity variable A and the maximum stimulation rate MSR form a further coordinate point of the characteristic curve K. Between these two coordinate points, the characteristic curve K has a linear course initially after the pacemaker is first put into operation. However, the course is varied in the context of an optimizing process in such a way that the frequency distribution function of the adaptive heart rate HR comes as close as possible to a physiologically appropriate reference curve. The optimized characteristic curve $K_{OPT}$, in the lower region of the variation range of the heart rate HR, has a lesser slope dHR/dA than does the linear characteristic curve K. As a result, lower heart rates HR occur more frequently in the optimized characteristic curve $K_{OPT}$. Correspondingly, the slope dHR/dA in the upper region of the variation range of the heart rate HR is greater in the optimized characteristic curve $K_{OPT}$ than in the linear characteristic curve K. High adaptive heart rates HR near the maximum stimulation rate MSR therefore occur more seldom in the optimized characteristic curve $K_{OPT}$.

Figure 3:
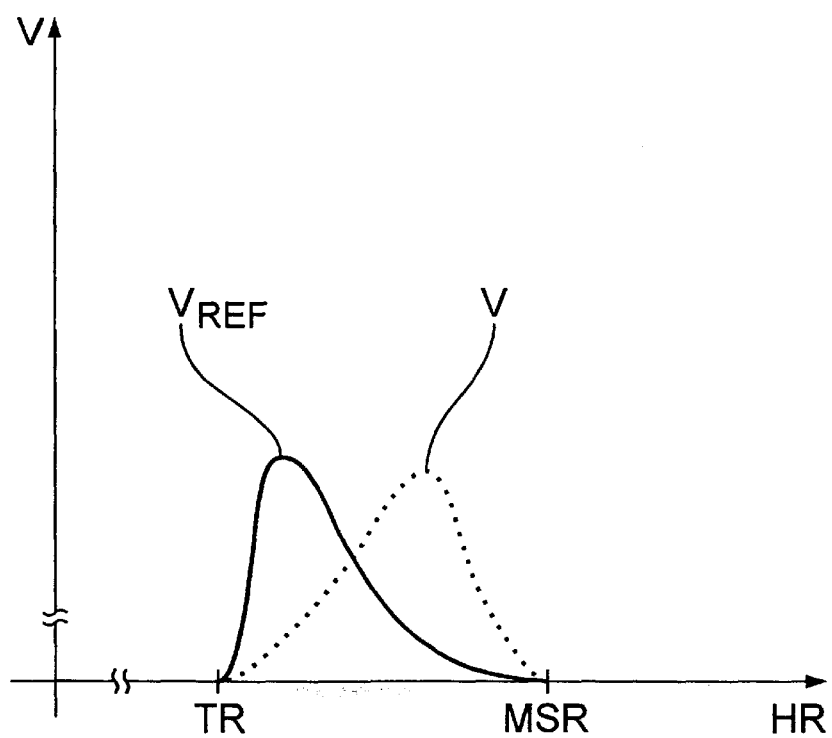
FIG. 3, the frequency distribution functions of the adaptive heart rate that result from the characteristic curves shown in FIG. 2.

FIG. 3 shows frequency distribution functions of the adaptive heart rate HR that can result from the characteristic curves K and $K_{OPT}$ shown in FIG. 2. The frequency distribution function V represents the distribution, resulting from the characteristic curve K, of the adaptive heart rate HR over the entire variation range of the heart rate HR from the base rate TR to the maximum stimulation rate MSR. The maximum frequency distribution function V is located in the upper frequency range near the maximum stimulation rate MSR; that is, the heart beats relatively often in the upper frequency range, which is physiologically inappropriate. The physiologically appropriate frequency distribution function of the adaptive heart rate is determined by the reference curve $V_{REF}$. The maximum point in the lower frequency range is near the base rate TR. The characteristic curve K of the characteristic curve member is set, by the principle sketched in FIG. 2, in such a way that the frequency distribution function V approaches the shape of the reference curve $V_{REF}$.

Figure 4:
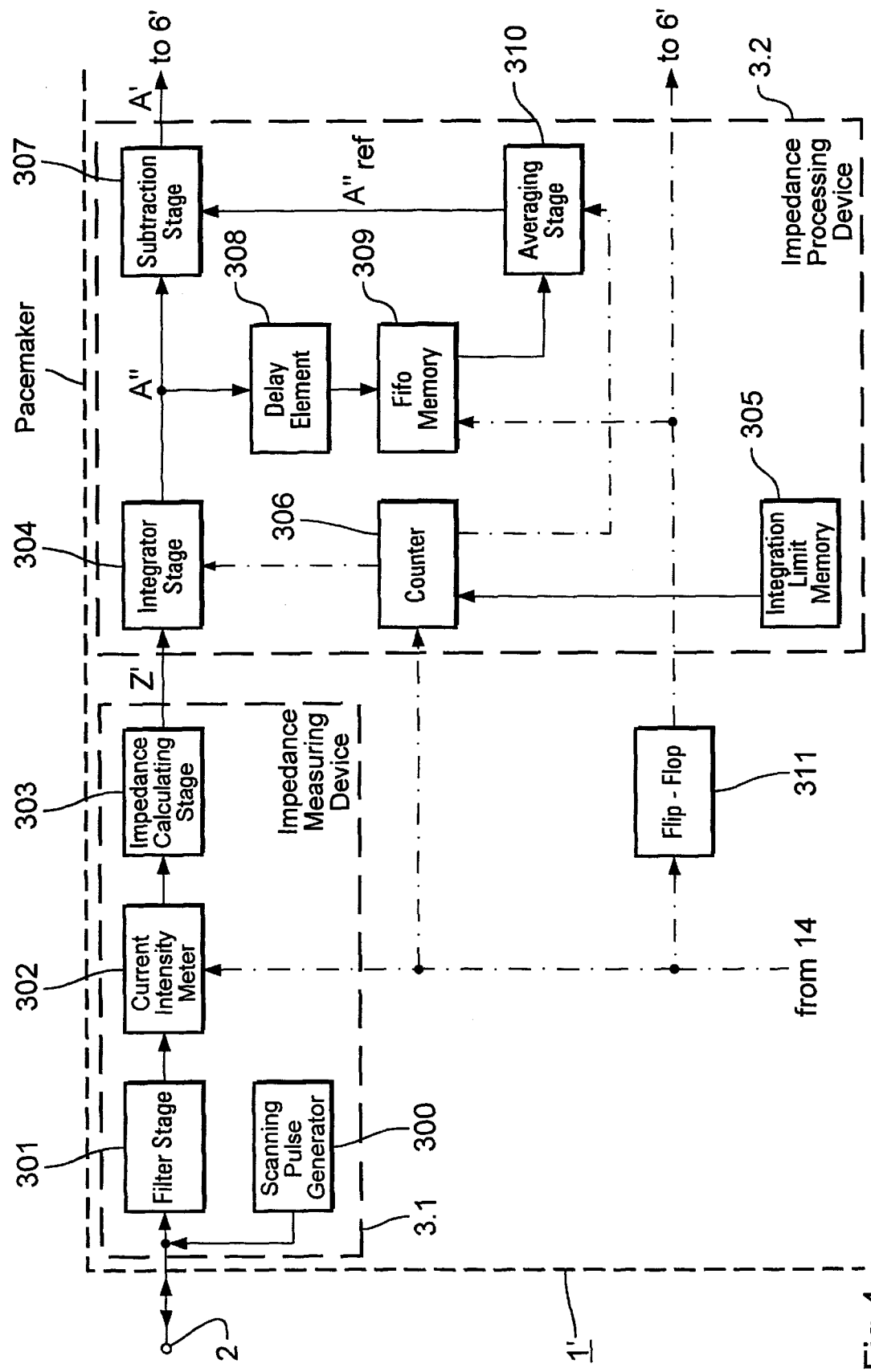
FIG. 4, an embodiment of an impedance measuring and processing device that can be used in a pacemaker similar to that shown in FIG. 1.

An expedient embodiment of the essential components for impedance measurement and processing of a pacemaker 1' modified slightly compared with FIG. 1 is shown in FIG. 4, in the form of a function block circuit diagram. In reliance on the reference numeral 3 selected in FIG. 1, the actual impedance measuring device is identified by reference numeral 3.1 and the impedance processing device by 3.2.

The impedance measuring device 3.1, connected on the input side to the intracardial measuring, sensing and stimulating electrode 2, includes in a design known per se a scanning pulse generator 300, a filter stage 301 for filtering out interfering signal components (originating from respiration, for instance), a current intensity meter 302, and an impedance calculating stage 303. The impedance measurements are clocked by the controller 14 (see FIG. 1) in synchronism with cardiac events to be stimulated, or spontaneous cardiac events.

The measurement signal Z' passes from the output of the impedance calculating stage 303 to the input of an integrator stage 304, in which a fixedly programmed number (8, for instance) of impedance measurement values from one cardiac cycle are subjected to integration. The number is permanently stored in an integration limit memory 305 and determines the counted value of a counter 306 that counts the measurement control pulses by the sequence controller 14 and that stops the integrator when the programmed number is reached. At the same time, the counter 306 trips the transfer of the result of integration A" to a subtraction stage 307 on the one hand and, via a delay element 308, to a FIFO memory 309 on the other.

In the memory 309, a predetermined number of impedance integral values from the past (for instance, from the last three minutes of pacemaker operation) is continuously stored in memory and by means of the output signal of the counter 306 are each transferred to an averaging stage 310 and subjected to current averaging.

The output signal of the averaging stage 310 is supplied as a reference value $A''_{ref}$ (along with the current impedance integral value as the primary impedance variable A") to the subtraction stage 307, which forms the difference between the current integral value and the current chronological average of the impedance variables as a reference value and outputs it as a secondary impedance variable A', which here represents the rate control parameter.

It should be noted that the signal connection, shown in FIG. 1, of the sequence controller 14 with the measuring electrode 2 with which the heart actions or intracardial ECGs are also detected, makes it possible to distinguish between spontaneous and evoked cardiac actions and hence enables erasure of the FIFO 309 if the event type changes, to which end a flip-flop 311 is provided, connected on its input side to the sequence controller 14 and on its output side to a delete input of the FIFO. The output signal of the flip-flop is also supplied to a modified rate determining device 6', where a rate offset is added to the calculated stimulation rate each time the event type changes, the amount of the rate offset being selected as a function of the preceding rate value and the current rate value such that the rate jump does not exceed a predetermined amount, and is returned over the course of the subsequent cardiac events in stages down to zero. The concrete circuitry means for realizing this additional function are available to one skilled in the art from known arrangements for rate smoothing or rate adaptation.

Further processing of the secondary impedance variable A' is otherwise equivalent to the explanation given for FIG. 1—except for the elimination of the differential member which is replaced by the components for forming the sliding average value.

In terms of how it is embodied, the invention is not limited to the preferred exemplary embodiments described above. On the contrary, a number of variants are conceivable that make use of the solution presented, even in fundamentally different types of embodiments.

In particular, the stage 3.2 may have many alternative embodiments, in which for instance the formation of a sliding average value as a reference value is replaced with time averaging with fixed starting points at predetermined time intervals, or can be performed on the basis of the output signals of the impedance calculating stage 303 instead of the output signals of the integrator stage 304, or in other words can be performed on the basis of pairs of (impedance, time) values. Instead of a fixedly predetermined number of impedance values to be integrated, a fixed chronological integration range may also be programmed. It is also advantageously possible to provide means for adjusting whichever integration range is valid at the time as a function of the signal of the motion sensor (or some other activity sensor).

I claim:

1. A rate-adaptive pacemaker comprising:
    an impedance measuring device for measuring a waveform over time of an intracardial impedance over at least a predetermined portion of one cardiac cycle;
    an impedance processing device for obtaining an impedance value from the waveform over time, the impedance processing device including:
        an integrator stage for determining a time integral of the impedance waveform over the predetermined portion of the cardiac cycle as a primary impedance value;
        an integral value memory coupled to the integrator stage for storing one reference integral value at a time, ascertained in at least one preceding cardiac cycle; and
        an arithmetic unit having inputs connected to outputs of the integrator stage and the integral value memory for calculating a secondary impedance value from the respective primary impedance value and from the reference integral value in accordance with a predetermined arithmetical equation; and
    a rate determining device, downstream of the impedance processing device and controlled by a sequence controller, for determining an adaptive stimulation rate on the basis of the secondary impedance value.

2. The rate-adaptive pacemaker of claim 1, wherein the arithmetic unit includes a subtraction stage for forming a differential value between the primary impedance value and the reference integral value, the differential value constituting the secondary impedance value.

3. The rate-adaptive pacemaker of claim 1, wherein the impedance processing device further includes a read only memory, connected at least indirectly to a control input of the integrator stage, for storing one of (a) limits of the predetermined portion of the cardiac cycle and (b) a location of impedance detection points on a time scale at which impedance values are sampled within the predetermined portion of the cardiac cycle.

4. The rate-adaptive pacemaker of claim 1, wherein the impedance processing device further includes a mean value forming stage including an input connected to the integral value memory and and an output connected to the arithmetic unit for forming a sliding mean value from preceding impedance measurements as a reference integral value.

5. The rate-adaptive pacemaker of claim 1, and further including a unipolar ventricle electrode connected to an input of the measuring device for being switched as both a sensing and stimulating electrode.

6. A rate-adaptive pacemaker comprising:
    an impedance measuring device for measuring a waveform over time of an intracardial impedance over at least a predetermined portion of one cardiac cycle;
    an impedance processing device for obtaining an impedance value from the waveform over time, the impedance processing device including an integrator stage for determining a time integral of the impedance waveform over the predetermined portion of the cardiac cycle as a primary impedance value and a read only memory, connected at least indirectly to a control input of the integrator stage, for storing one of (a) limits of the predetermined portion of the cardiac cycle and (b) a location of impedance detection points on a time scale at which impedance values are sampled within the predetermined portion of the cardiac cycle; and
    a rate determining device, downstream of the impedance processing device and controlled by a sequence controller for determining an adaptive stimulation rate using the primary impedance value.

7. The rate-adaptive pacemaker of claim 6, wherein the impedance processing device further includes a read only memory, connected at least indirectly to a control input of the integrator stage, for storing one of (a) limits of the predetermined portion of the cardiac cycle and (b) a location of impedance detection points on a time scale at which impedance values are sampled within the predetermined portion of the cardiac cycle.

8. The rate-adaptive pacemaker of claim 6, wherein the rate determining device includes a differential member having a data input for the primary impedance value.

9. The rate-adaptive pacemaker of claim 6, and further including a unipolar ventricle electrode connected to an input of the measuring device for being switched as both a sensing and stimulating electrode.

10. A rate-adaptive pacemaker comprising:
    an impedance measuring device for measuring a waveform over time of an intracardial impedance over at least a predetermined portion of one cardiac cycle;
    an impedance processing device for obtaining an impedance value from the waveform over time, the impedance processing device including an integrator stage for determining a time integral of the impedance waveform over the predetermined portion of the cardiac cycle as a primary impedance value;
    a differential member including a data input for receiving the impedance value at an output of the integrator stage and including a control input for setting a time constant of the differential member;
    a digital motion sensor for an activity variable having an output coupled to the control input of differential stage, the output of the sensor assuming a first state when a patient is resting and assuming a second state when the patient is in motion so that the time constant of the differential member is set to a differential time ($T_D$) value that is substantially lower when the patient is resting than when the patient is in motion; and a rate determining device, downstream of the impedance processing device and controlled by a sequence controller, for determining an adaptive stimulation rate using the primary impedance value.

11. The rate-adaptive pacemaker of claim 9, wherein the impedance processing device further includes a read only memory, connected at least indirectly to a control input of the integrator stage, for storing one of (a) limits of the predetermined portion of the cardiac cycle and (b) a location of impedance detection points on a time scale at which impedance values are sampled within the predetermined portion of the cardiac cycle.

12. The rate-adaptive pacemaker of claim 10, and further including a unipolar ventricle electrode connected to an input of the measuring device for being switched as both a sensing and stimulating electrode.

* * * * *